US010038952B2

(12) United States Patent
Labrosse et al.

(10) Patent No.: US 10,038,952 B2
(45) Date of Patent: Jul. 31, 2018

(54) SOUND MANAGEMENT SYSTEMS FOR IMPROVING WORKPLACE EFFICIENCY

(71) Applicant: STIRWORKS INC., Pasadena, CA (US)

(72) Inventors: Jean-Paul Labrosse, Altadena, CA (US); Scott Sullivan, San Francisco, CA (US); Matthew N. Schneider, Sierra Madre, CA (US)

(73) Assignee: STEELCASE INC., Grand Rapids, MI (US)

( * ) Notice: Subject to any disclaimer, the term of this patent is extended or adjusted under 35 U.S.C. 154(b) by 0 days.

(21) Appl. No.: 14/612,302

(22) Filed: Feb. 3, 2015

(65) Prior Publication Data
US 2015/0222989 A1 Aug. 6, 2015

Related U.S. Application Data

(60) Provisional application No. 61/935,343, filed on Feb. 4, 2014.

(51) Int. Cl.
H04R 1/10 (2006.01)
A61M 21/02 (2006.01)
(Continued)

(52) U.S. Cl.
CPC .......... *H04R 1/1083* (2013.01); *A61M 21/02* (2013.01); *A61B 5/01* (2013.01); *A61B 5/021* (2013.01);
(Continued)

(58) Field of Classification Search
CPC ... G06F 17/30764; H04R 1/10; H04R 1/1083; H04R 2460/01; H04R 2460/03;
(Continued)

(56) References Cited

U.S. PATENT DOCUMENTS 3,953,770 A 4/1976 Hayashi
4,163,929 A 8/1979 Janu et al.
(Continued)

FOREIGN PATENT DOCUMENTS

CN 202286910 U 7/2012
DE 19604329 A1 8/1997
(Continued)

OTHER PUBLICATIONS

Anthro Corporation, Can Anthro "Walk the Talk"?: Employees Embark on a 30-Day Sit-Stand Challenge, Press Release Oct. 11, 2010, www.anthro.com/press-releases/2010/employees-embark-on-a-30-day-sit-stand-challenge, copyright 2016, 4 pages.
(Continued)

*Primary Examiner* — Vivian Chin
*Assistant Examiner* — Jason R Kurr
(74) *Attorney, Agent, or Firm* — Quarles & Brady LLP

(57) ABSTRACT

A sound management system for use by a user located within an environment includes a memory device for storing a selection of sounds. The sounds can be music and/or various "colors" of noise (e.g., white, pink, and brown). A controller is used to select one particular stored sound based on a measured biological condition of the user, such as stress or fatigue, or an environmental condition of the environment, such as ambient noise. According to one embodiment, the system is used in conjunction with a sit/stand desk and the sound selection is made in response to changes in the desk height. The selected sound is selected to help abate or mitigate distracting sounds in the environment, such as people talking. The selected sounds are played to the user through headphones worn by the user, or through nearby speakers.

32 Claims, 1 Drawing Sheet

(51) Int. Cl.
<table>
<tr><td>A61B 5/01</td><td>(2006.01)</td></tr>
<tr><td>A61B 5/021</td><td>(2006.01)</td></tr>
<tr><td>A61B 5/024</td><td>(2006.01)</td></tr>
<tr><td>A61M 21/00</td><td>(2006.01)</td></tr>
</table>

(52) U.S. Cl.
CPC ...... *A61B 5/024* (2013.01); *A61M 2021/0027* (2013.01); *A61M 2230/06* (2013.01); *A61M 2230/30* (2013.01); *A61M 2230/50* (2013.01); *H04R 2460/01* (2013.01); *H04R 2460/13* (2013.01)

(58) Field of Classification Search
CPC . H04R 2460/13; G10K 11/175; A61M 21/02; A61M 2021/0027; A61M 2230/06; A61M 2230/30; A61M 2230/50; A61B 5/01; A61B 5/021; A61B 5/024; A47B 21/00; A47B 21/02
USPC ............................................ 381/73.1; 700/94
See application file for complete search history.

(56) References Cited

U.S. PATENT DOCUMENTS

| | | | |
|---|---|---|---|
| 4,440,096 A | 4/1984 | Rice et al. | |
| 4,571,682 A | 2/1986 | Silverman et al. | |
| 4,779,865 A | 10/1988 | Lieberman et al. | |
| 4,821,118 A | 4/1989 | Lafreniere | |
| 4,828,257 A | 5/1989 | Dyer et al. | |
| 4,849,733 A * | 7/1989 | Conigliaro | B60R 22/48 |
| | | | 340/457.1 |
| 4,894,600 A | 1/1990 | Kearney | |
| 5,019,950 A | 5/1991 | Johnson | |
| 5,022,384 A | 6/1991 | Freels et al. | |
| 5,140,977 A | 8/1992 | Raffel | |
| 5,224,429 A | 7/1993 | Borgman et al. | |
| 5,259,326 A | 11/1993 | Borgman et al. | |
| 5,305,238 A | 4/1994 | Starr, III et al. | |
| 5,308,296 A | 5/1994 | Eckstein | |
| 5,323,695 A | 6/1994 | Borgman et al. | |
| 5,335,188 A | 8/1994 | Brisson | |
| 5,371,693 A | 12/1994 | Nakazoe | |
| 5,412,297 A | 5/1995 | Clark et al. | |
| 5,435,799 A | 7/1995 | Lundin | |
| 5,456,648 A | 10/1995 | Edinburg et al. | |
| 5,583,831 A | 12/1996 | Churchill et al. | |
| 5,612,869 A | 3/1997 | Letzt et al. | |
| 5,666,426 A * | 9/1997 | Helms | H03G 3/32 |
| | | | 381/104 |
| 5,765,910 A | 6/1998 | Larkin et al. | |
| 5,853,005 A | 12/1998 | Scanlon | |
| 5,870,647 A | 2/1999 | Nada et al. | |
| 5,890,997 A | 4/1999 | Roth | |
| 5,944,633 A | 8/1999 | Wittrock | |
| 6,013,008 A | 1/2000 | Fukushima | |
| 6,014,572 A | 1/2000 | Takahashi | |
| 6,030,351 A | 2/2000 | Schmidt et al. | |
| 6,032,108 A | 2/2000 | Sciple et al. | |
| 6,075,755 A | 6/2000 | Zarchan | |
| 6,135,951 A | 10/2000 | Richardson et al. | |
| 6,142,910 A | 11/2000 | Heuvelman | |
| 6,161,095 A | 12/2000 | Brown | |
| 6,286,441 B1 | 9/2001 | Burdi et al. | |
| 6,296,408 B1 | 10/2001 | Larkin et al. | |
| 6,312,363 B1 | 11/2001 | Watterson et al. | |
| 6,360,675 B1 | 3/2002 | Jones | |
| 6,447,424 B1 | 9/2002 | Ashby et al. | |
| 6,458,060 B1 | 10/2002 | Watterson et al. | |
| 6,527,674 B1 | 3/2003 | Clem | |
| 6,595,144 B1 | 7/2003 | Doyle | |
| 6,622,116 B2 | 9/2003 | Skinner et al. | |
| 6,669,286 B2 | 12/2003 | Iusim | |
| 6,702,719 B1 | 3/2004 | Brown et al. | |
| 6,716,139 B1 | 4/2004 | Hosseinzadeh-Dolkhani et al. | |
| 6,746,371 B1 | 6/2004 | Brown et al. | |
| 6,749,537 B1 | 6/2004 | Hickman | |
| 6,790,178 B1 | 9/2004 | Mault et al. | |
| 6,793,607 B2 | 9/2004 | Neil | |
| 6,964,370 B1 | 11/2005 | Hagale et al. | |
| 6,977,476 B2 | 12/2005 | Koch | |
| 6,987,221 B2 * | 1/2006 | Platt | G06F 17/30038 |
| | | | 700/94 |
| 7,030,735 B2 | 4/2006 | Chen | |
| 7,063,644 B2 | 6/2006 | Albert et al. | |
| 7,070,539 B2 | 7/2006 | Brown et al. | |
| 7,128,693 B2 | 10/2006 | Brown et al. | |
| 7,141,026 B2 | 11/2006 | Aminian et al. | |
| 7,161,490 B2 | 1/2007 | Huiban | |
| 7,172,530 B1 | 2/2007 | Hercules | |
| 7,301,463 B1 | 11/2007 | Paterno | |
| 7,327,442 B1 | 2/2008 | Fear et al. | |
| 7,439,956 B1 | 10/2008 | Albouyeh et al. | |
| 7,510,508 B2 | 3/2009 | Santomassimo et al. | |
| 7,523,905 B2 | 4/2009 | Timm et al. | |
| 7,538,284 B2 | 5/2009 | Nielsen et al. | |
| 7,594,873 B2 | 9/2009 | Terao et al. | |
| 7,614,001 B2 | 11/2009 | Abbott et al. | |
| 7,628,737 B2 | 12/2009 | Kowallis et al. | |
| 7,635,324 B2 | 12/2009 | Balis | |
| 7,637,847 B1 | 12/2009 | Hickman | |
| 7,640,866 B1 | 1/2010 | Schermerhorn | |
| 7,652,230 B2 | 1/2010 | Baier | |
| 7,661,292 B2 | 2/2010 | Buitmann et al. | |
| 7,717,827 B2 | 5/2010 | Kurunmaki et al. | |
| 7,722,503 B1 | 5/2010 | Smith et al. | |
| 7,735,918 B2 | 6/2010 | Beck | |
| 7,857,731 B2 | 12/2010 | Hickman et al. | |
| 7,884,808 B2 | 2/2011 | Joo | |
| 7,892,148 B1 | 2/2011 | Stauffer et al. | |
| 7,909,737 B2 | 3/2011 | Ellis et al. | |
| 7,914,468 B2 | 3/2011 | Shalon et al. | |
| 7,931,563 B2 | 4/2011 | Shaw et al. | |
| 7,955,219 B2 | 6/2011 | Birrell et al. | |
| 8,001,472 B2 | 8/2011 | Gilley et al. | |
| 8,024,202 B2 | 9/2011 | Carroll et al. | |
| 8,047,966 B2 | 11/2011 | Dorogusker et al. | |
| 8,051,782 B2 | 11/2011 | Nethken et al. | |
| 8,052,580 B2 | 11/2011 | Saalasti et al. | |
| 8,092,346 B2 | 1/2012 | Shea | |
| 8,105,209 B2 | 1/2012 | Lannon et al. | |
| 8,109,858 B2 | 2/2012 | Redmann | |
| 8,159,335 B2 | 4/2012 | Cox, Jr. | |
| 8,167,776 B2 | 5/2012 | Lannon et al. | |
| 8,206,325 B1 | 6/2012 | Najafi et al. | |
| 8,257,228 B2 | 9/2012 | Quatrochi et al. | |
| 8,361,000 B2 | 1/2013 | Gaspard | |
| 8,381,603 B2 | 2/2013 | Peng et al. | |
| 8,432,356 B2 | 4/2013 | Chase | |
| 8,462,921 B2 | 6/2013 | Parker | |
| 8,522,695 B2 | 9/2013 | Ellegaard | |
| 8,540,641 B2 | 9/2013 | Kroll et al. | |
| 8,550,820 B2 | 10/2013 | Soltanoff | |
| 8,560,336 B2 | 10/2013 | Schwarzberg et al. | |
| 8,593,286 B2 | 11/2013 | Razoumov et al. | |
| 8,595,023 B2 | 11/2013 | Kirchhoff et al. | |
| 8,620,617 B2 | 12/2013 | Yuen et al. | |
| 8,668,045 B2 | 3/2014 | Cohen | |
| 8,688,467 B2 | 4/2014 | Harrison et al. | |
| 8,690,578 B1 | 4/2014 | Nusbaum et al. | |
| 8,690,735 B2 | 4/2014 | Watterson et al. | |
| 8,700,690 B2 | 4/2014 | Raghav et al. | |
| 8,771,222 B2 | 7/2014 | Kanderian, Jr. et al. | |
| 8,812,096 B2 | 8/2014 | Flaherty et al. | |
| 8,814,754 B2 | 8/2014 | Weast et al. | |
| 8,818,782 B2 | 8/2014 | Thukral et al. | |
| 8,821,350 B2 | 9/2014 | Maertz | |
| 8,825,482 B2 | 9/2014 | Hernandez-Abrego et al. | |
| 8,836,500 B2 | 9/2014 | Houvener et al. | |
| 8,847,988 B2 | 9/2014 | Geisner et al. | |
| 8,947,215 B2 | 2/2015 | Mandel et al. | |
| 8,965,541 B2 | 2/2015 | Martinez et al. | |
| 8,984,685 B2 | 3/2015 | Robertson et al. | |
| 8,997,588 B2 | 4/2015 | Taylor | |

(56) References Cited

U.S. PATENT DOCUMENTS

| | | |
|---|---|---|
| 9,049,923 B1 * | 6/2015 | Delagey .................. A47B 9/18 |
| 9,084,475 B2 | 7/2015 | Hjelm |
| 9,119,568 B2 | 9/2015 | Yin et al. |
| 9,167,894 B2 | 10/2015 | DesRoches et al. |
| 9,236,817 B2 | 1/2016 | Strothmann et al. |
| 9,486,070 B2 | 11/2016 | Labrosse et al. |
| 2001/0013307 A1 | 8/2001 | Stone |
| 2001/0028308 A1 | 10/2001 | De La Huerga |
| 2002/0055419 A1 | 5/2002 | Hinnebusch |
| 2002/0145512 A1 | 10/2002 | Sleichter, III et al. |
| 2004/0010328 A1 | 1/2004 | Carson et al. |
| 2004/0014014 A1 | 1/2004 | Hess |
| 2004/0229729 A1 | 11/2004 | Albert et al. |
| 2004/0239161 A1 | 12/2004 | Lee |
| 2005/0058970 A1 | 3/2005 | Perlman et al. |
| 2005/0113649 A1 | 5/2005 | Bergantino |
| 2005/0165626 A1 | 7/2005 | Karpf |
| 2005/0172311 A1 | 8/2005 | Hjelt et al. |
| 2005/0182653 A1 | 8/2005 | Urban et al. |
| 2005/0202934 A1 | 9/2005 | Olrik et al. |
| 2005/0209051 A1 | 9/2005 | Santomassimo et al. |
| 2006/0063980 A1 | 3/2006 | Hwang et al. |
| 2006/0205564 A1 | 9/2006 | Peterson |
| 2006/0241520 A1 | 10/2006 | Robertson |
| 2006/0250524 A1 | 11/2006 | Roche |
| 2006/0266791 A1 | 11/2006 | Koch et al. |
| 2007/0135264 A1 | 6/2007 | Rosenberg |
| 2007/0179355 A1 | 8/2007 | Rosen |
| 2007/0200396 A1 | 8/2007 | Baumann et al. |
| 2007/0219059 A1 | 9/2007 | Schwartz et al. |
| 2007/0265138 A1 | 11/2007 | Ashby |
| 2008/0030317 A1 | 2/2008 | Bryant |
| 2008/0045384 A1 | 2/2008 | Matsubara et al. |
| 2008/0051256 A1 | 2/2008 | Ashby et al. |
| 2008/0077620 A1 | 3/2008 | Gilley et al. |
| 2008/0098525 A1 | 5/2008 | Doleschal et al. |
| 2008/0132383 A1 | 6/2008 | Einav et al. |
| 2008/0245279 A1 | 10/2008 | Pan |
| 2008/0255794 A1 | 10/2008 | Levine |
| 2008/0256445 A1 | 10/2008 | Olch |
| 2008/0300914 A1 | 12/2008 | Karkanias et al. |
| 2008/0304365 A1 | 12/2008 | Jarvis et al. |
| 2008/0306351 A1 | 12/2008 | Izumi |
| 2009/0076335 A1 | 3/2009 | Schwarzberg et al. |
| 2009/0078167 A1 | 3/2009 | Ellegaard |
| 2009/0132579 A1 | 5/2009 | Kwang |
| 2009/0156363 A1 | 6/2009 | Guidi et al. |
| 2009/0195393 A1 | 8/2009 | Tegeler |
| 2009/0229475 A1 | 9/2009 | Bally et al. |
| 2009/0270227 A1 | 10/2009 | Ashby et al. |
| 2009/0273441 A1 | 11/2009 | Mukherjee |
| 2010/0049008 A1 | 2/2010 | Doherty et al. |
| 2010/0073162 A1 | 3/2010 | Johnson et al. |
| 2010/0135502 A1 * | 6/2010 | Keady .................. A61B 5/121 381/58 |
| 2010/0185398 A1 | 7/2010 | Berns et al. |
| 2010/0198374 A1 | 8/2010 | Carson et al. |
| 2010/0201201 A1 | 8/2010 | Mobarhan et al. |
| 2010/0205542 A1 | 8/2010 | Walman |
| 2010/0234184 A1 | 9/2010 | Le Page et al. |
| 2010/0323846 A1 | 12/2010 | Komatsu et al. |
| 2011/0015041 A1 | 1/2011 | Shea |
| 2011/0015495 A1 | 1/2011 | Dothie et al. |
| 2011/0033830 A1 | 2/2011 | Cherian |
| 2011/0054359 A1 | 3/2011 | Sazonov et al. |
| 2011/0080290 A1 | 4/2011 | Baxi et al. |
| 2011/0104649 A1 | 5/2011 | Young et al. |
| 2011/0120351 A1 | 5/2011 | Shoenfeld |
| 2011/0182438 A1 * | 7/2011 | Koike .................. G10L 21/04 381/73.1 |
| 2011/0184748 A1 | 7/2011 | Fierro et al. |
| 2011/0245979 A1 | 10/2011 | Koch |
| 2011/0275939 A1 | 11/2011 | Walsh et al. |
| 2011/0281248 A1 | 11/2011 | Feenstra et al. |
| 2011/0281687 A1 | 11/2011 | Gilley et al. |
| 2011/0296306 A1 | 12/2011 | Oddsson et al. |
| 2012/0015779 A1 | 1/2012 | Powch et al. |
| 2012/0051579 A1 | 3/2012 | Cohen |
| 2012/0116550 A1 | 5/2012 | Hoffman et al. |
| 2012/0173319 A1 | 7/2012 | Ferrara |
| 2012/0316661 A1 * | 12/2012 | Rahman ................ G06F 1/1694 700/94 |
| 2013/0002533 A1 | 1/2013 | Burroughs et al. |
| 2013/0012788 A1 | 1/2013 | Horseman |
| 2013/0116092 A1 | 5/2013 | Martinez et al. |
| 2013/0144470 A1 | 6/2013 | Ricci |
| 2013/0199419 A1 | 8/2013 | Hjelm |
| 2013/0199420 A1 | 8/2013 | Hjelm |
| 2013/0207889 A1 | 8/2013 | Chang et al. |
| 2013/0218309 A1 | 8/2013 | Napolitano |
| 2013/0316316 A1 | 11/2013 | Flavell et al. |
| 2013/0331993 A1 | 12/2013 | Detsch et al. |
| 2014/0096706 A1 | 4/2014 | Labrosse et al. |
| 2014/0137773 A1 * | 5/2014 | Mandel ................ G06Q 10/109 108/50.11 |
| 2014/0156645 A1 | 6/2014 | Brust et al. |
| 2014/0245932 A1 * | 9/2014 | McKenzie, III ....... A47B 21/02 108/50.01 |
| 2014/0249853 A1 * | 9/2014 | Proud .................... G06Q 50/24 705/3 |
| 2014/0270254 A1 * | 9/2014 | Oishi ...................... H04R 3/04 381/98 |
| 2015/0064671 A1 | 3/2015 | Murville et al. |
| 2015/0071453 A1 * | 3/2015 | Po ........................ G10K 11/175 381/71.11 |
| 2015/0142381 A1 * | 5/2015 | Fitzsimmons ......... A47C 7/006 702/166 |
| 2015/0302150 A1 | 10/2015 | Mazar et al. |
| 2016/0051042 A1 | 2/2016 | Koch |
| 2016/0309889 A1 | 10/2016 | Lin et al. |
| 2017/0052517 A1 | 2/2017 | Tsai et al. |
| 2017/0135636 A1 * | 5/2017 | Park ...................... A61B 5/681 |

FOREIGN PATENT DOCUMENTS

| | | |
|---|---|---|
| DE | 10260478 A1 | 7/2004 |
| DE | 102008044848 A1 | 3/2010 |
| DE | 202014005160 U1 | 7/2014 |
| EP | 1159989 A1 | 12/2001 |
| EP | 1470766 A1 | 10/2004 |
| GB | 2424084 A | 9/2006 |
| JP | H11178798 A | 7/1999 |
| JP | 2001289975 A | 10/2001 |
| JP | 2005267491 A | 9/2005 |
| SE | 516479 C2 | 1/2002 |
| WO | 0219603 A2 | 3/2002 |
| WO | 02062425 A1 | 8/2002 |
| WO | 2005032363 A1 | 4/2005 |
| WO | 2005074754 A1 | 8/2005 |
| WO | 2006042415 A1 | 4/2006 |
| WO | 2006042420 A1 | 4/2006 |
| WO | 2006065679 A2 | 6/2006 |
| WO | 2007099206 A1 | 9/2007 |
| WO | 2008008729 A2 | 1/2008 |
| WO | 2008050590 A1 | 2/2008 |
| WO | 2008101085 A2 | 8/2008 |
| WO | 2010019644 A2 | 2/2010 |
| WO | 2010023414 A1 | 3/2010 |
| WO | 2011133628 A1 | 10/2011 |
| WO | 2012061438 A2 | 5/2012 |
| WO | 2012108938 A1 | 8/2012 |
| WO | 2013033788 A1 | 3/2013 |

OTHER PUBLICATIONS

Benallal, et al., A Simple Algorithm for Object Location from a Single Image Without Camera Calibration, In International Conference on Computational Science and Its Applications, pp. 99-104. Springer Berlin Heidelberg, 2003.

Bendixen, et al., Pattern of Ventilation in Young Adults, Journal of Applied Physiology, 1964, 19(2):195-198.

(56) References Cited

OTHER PUBLICATIONS

BrianLaF, asp.net 4.0 TimePicker User Control, www.codeproject.com/articles/329011/asp-net-timepicker-user-control, Feb. 25, 2012, 5 pages.
EJAZ, Time Picker Ajax Extender Control, www.codeproject.com/articles/213311/time-picker-ajax-extender-control, Jun. 22, 2011, 8 pages.
Heddings, Stop Hitting Snooze: Change the Default Reminder Time for Outlook Appointments, www.howtogeek.com/howto/microsoft-office/stop-hitting-snooze-change-the-default-reminder-time-for-outlook-appointments, Apr. 25, 2008, 2 pages.
Hopkins Medicine, Vital Signs (Body Temperature, Pulse Rate, Respiration Rate, Blood Pressure). Source: Johns Hopkins Medicine Health Library, 2016, pp. 1-4.
Kriebel, How to Create a Two-Panel Column Chart in Tableau (And Save Lots of Time Compared to Excel), www.vizwiz.com/2012/02/how-to-create-two-panel-column-chart-in.html, 2012, 14 pages.
Microsoft, Automatically Adjust the Start and Finish Dates for New Projects, Applies To: Project 2007, Project Standard 2007, https://support.office.com/en-us/article/Automatically-adjust-the-start-and-finish-dates-for-new-projects-27c57cd1-44f3-4ea8-941a-dc5d56bdc540?ui=en-US&rs=en-US&ad=US&fromAR=1, Copyright 2017 Microsoft.
mrexcel.com, Forum: How to Calculate Percentage of Total Used Time, www.mrexcel.com/forum/excel-qestions/192521-how-calculate-percentage-total-used-time.html., Post Date: Mar. 20, 2006, 4 pages.
Paolo, Arduino Forum, Measuring Point To Point Distances With Accelerometer, http://forum.arduino.cc/index.php?action=printpage;topic=49902.0;images, Post Date: Jan. 26, 2011, 5 pages.
Process Dash, Using the Task & Schedule Tool, www.processdash.com/static/help/Topics/Planning/UsingTaskSchedule.html, Mar. 4, 2011.
Sun Microsystems, Lights Out Management Module, https://docs.oracle.com/cd/E19585-01/819-0445-10/lights_out.html, Copyright 2004, Sun Microsystems, Inc.
Wideman, Issues Regarding Total Time and Stage 1 Time, http://maxwideman.com/papers/resource/issues.html, 1994.
LINAK, Deskline Controls/Handsets User Manual, Copyright LINAK 2017.
LINAK, DPG Desk Panels—A New Way to Adjust Your Office Desk, Product News, May 19, 2017.
Steelcase, Inc., Airtouch Height-Adjustable Tables, Brochure, Copyright 2015 Steelcase Inc.
Steelcase, Inc., Migration Height-Adjustable Desk, Brochure, Copyright 2015 Steelcase Inc.
Steelcase, Inc., Ology Height-Adjustable Desk, Brochure, Copyright 2016 Steelcase Inc.
Steelcase, Inc., Series 5 Sit-To-Stand Height-Adjustable Tables, Brochure, Copyright 2015 Steelcase Inc.
Steelcase, Inc., Series 7 Enhanced Sit-To-Stand Height-Adjustable Tables, Brochure, Copyright 2015 Steelcase Inc.
Linak, Deskline Deskpower DB4/DL4 Systems User Manual, Copyright Linak 2007.
Linak, Deskline DL9/DB9/DL11 System User Manual, Copyright Linak 2007.
Office Details, Inc., Height AdjusTable Worksurfaces User Instructions, Copyright 2004 Office Details Inc.

* cited by examiner

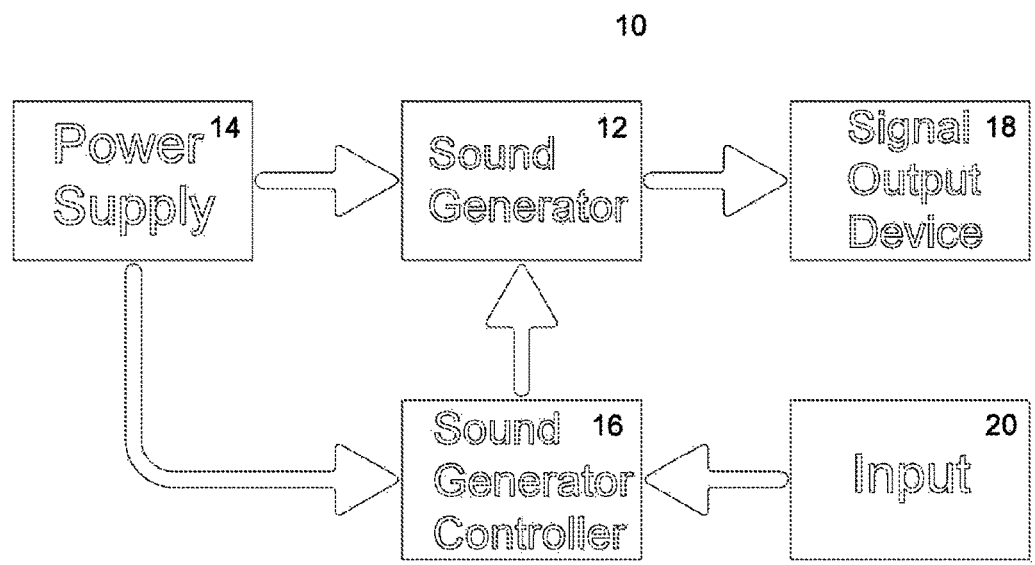

SOUND MANAGEMENT SYSTEMS FOR IMPROVING WORKPLACE EFFICIENCY

CROSS-REFERENCE TO RELATED APPLICATION

This application claims the benefit of U.S. Provisional Application No. 61/935,343, filed Feb. 4, 2014, entitled "Sound Management Systems for Improving Workplace Efficiency."

BACKGROUND OF THE INVENTION

1) Field of the Invention

The present invention generally relates to devices and systems for benefiting the health and efficiency of workers in a workplace, and more particularly, to systems and devices for the purpose of mitigating or otherwise controlling unwanted conversation and also managing structured sounds (music) and random sounds generated within a workplace.

2) Discussion of Related Art

Today's workplace environments often include "open spaces" wherein many employees get to enjoy working in close proximity to each other in spaces that are generally replete of barriers, such as cubical walls. This open working arrangement is supposed to provide a means for the sharing ideas and collaboration which is supposed to improve work efficiency and creativity. It has the additional benefit of saving expenses by maximizing floor space and simplifying the lighting requirements for everyone, but unfortunately not everyone can work so efficiently in such an open environment and for many people, work efficiency and even morale can "take a hit."

People are different and many people just need their space and don't appreciate sharing with others and don't appreciate the many distractions that have become common in such open space environments. One such distraction is sound, both general office noises (a nearby photocopier) and other people's conversations. People need to concentrate and many cannot unless they can control the sounds within their work area. If two people seated next to a worker, for example, start a conversation with each other, the worker's brain will involuntarily listen-in and try to comprehend what is being said nearby. This often confuses the worker and his or her concentration and work efficiency plummets, that is until the conversation stops.

In an effort to maintain the benefits of an open-space layout for a workplace and help control noise and regional intelligible conversations, two basic sound-management systems have been developed, sound-cancellation and sound-masking.

Sound cancellation—or "active noise control"—electronically changes a received incoming sound signal within an environment to minimize the signal before it can be received by a human's ear. With sound cancellation, a sound signal is first received by a microphone that has been placed within a subject environment. The signal analyzed by a microprocessor and then an inverted signal (mirror image) is sent to a speaker that has been positioned within the environment. The speaker broadcasts the exact opposite of the original sound signal, thus flattening out the original sound signal, effectively cancelling it. The end result is that the worker located within the environment will hear very little background sounds.

Unfortunately, sound cancellation works best in a very controlled and small environment that has a uniform, consistent, and predictable shape. Therefore, such sound cancellation systems work best with headphones and are not suitable for controlling the many dynamic frequencies common in open areas, such as within a large room that includes a myriad of sources of sounds, moving objects and complex and unpredictable shapes of all sizes. Any attempt to mitigate the background sounds in such a complex environment would require massive processors and a multitude of microphones and speakers. This would be prohibitively expensive and still would likely only produce marginal sound-control within the environment.

Sound masking, on the other hand, works on the principle that when background noise is added to an environment, speech becomes less intelligible. The "Articulation Index" (or "AI"), which is a measurement of intelligible speech is controlled within the environment. In order for sound masking to be effective, the AI must be lowered by a change in the signal-to-noise ratio. The "signal" is typically a person speaking within the environment, and the "noise" is the sound masking signal.

A high signal-to-noise ratio means that speech within the environment is very intelligible and the workers will suffer by not being able to concentrate. By simply introducing select sounds (controlled noise) to the environment, the signal to noise ratio can be reduced significantly, to the point that the voices carried by anyone speaking within a subject environment will become unintelligible a short distance away so that even nearby workers will not become distracted and work efficiency will presumably remain unaffected. The generated noise used in such sound-masking systems is typically what is referred to as "white noise", but so-called "pink noise" can be applied as will.

To be effective, sound masking systems must generate sound that is both random and within a specific range of frequency and decibels. The human brain will actively process received sounds in which it can identify a recognizable pattern, such as speech, but will quickly tune out sounds it cannot make sense of, such as static sounds. Sound masking works by injecting a random, low-level background noise within the environment that correlates in frequency to human speech. Control of the decibel level and frequency of the generated noise (white or pink) within the environment is critical. The noise should be just loud enough to make it difficult to understand conversations a predetermined distance away. However, should the noise become too loud, the human brain will no longer ignore it and the noise will begin to interfere with other human processing, such as working. Care must be taken to insure that both the decibel level and the frequency of the sound masking system is appropriate for the particular environment. This is what a "white noise" system does to mask sound it basically "fills in" the sound spectrum around you with barely perceptible "unstructured" noise. The sounds of running water serve well as white noise because the sounds are able to mask human speech very well, without distracting or annoying a listener. The running water sound creates a random, yet relatively uniform sound wave, within a specific frequency spectrum.

Early sound-masking systems installed in buildings in the 1960s simulated the sound of air moving by electronically filtering random noise produced by gas-discharge vacuum tubes. Loudspeakers in the ceiling distributed the amplified noise signal throughout the office. However, making human speech unintelligible required a volume level so high that the sound masking itself became a distracting annoyance.

In the 1970s, electronically generated sound masking employed frequency generators that shaped sound to better mask speech became more practical and worked well when installed correctly. In the 1980s, researchers began using 1/f noise, the phenomenon also known as "flicker" or "pink" noise. Calibrating this "pink" noise to match the frequencies of human speech raised the threshold of audibility just enough to mask intelligibility without requiring the higher volumes used in earlier systems.

Music and Headphones:

Although the above sound masking techniques may work well in many situations, many people just cannot listen to the sounds of "ocean waves" all day long. It is not uncommon for workers to simply play some music through their headphones to help create a controlled sound environment and effectively mask surrounding sounds. Unfortunately, even a preset playlist of songs may not also match a particular user's need throughout a day.

Although many of the above-described sound masking systems work generally well, Applicants have recognized areas of improvement with such systems.

OBJECTS OF THE INVENTION

It is therefore a first object of the invention to overcome the deficiencies of the prior art.

It is another object of the invention to provide a useful, effective sound masking system that can be altered automatically in response to select inputs.

It is another object of the invention to provide a sound controller for controlling the sounds played to a user in response to select inputs.

SUMMARY OF THE INVENTION

A sound management system for use by a user located within an environment includes a memory device for storing a selection of sounds. The sounds can be music and/or various "colors" of noise (e.g., white, pink, and brown). A controller is used to select one particular stored sound based on a measured biological condition of the user, such as stress or fatigue, or an environmental condition of the environment, such as ambient noise. According to one embodiment, the system is used in conjunction with a sit/stand desk and the sound selection is made in response to changes in the desk height. The selected sound is selected to help abate or mitigate distracting sounds in the environment, such as people talking. The selected sounds are played to the user through headphones worn by the user, or through nearby speakers.

BRIEF DESCRIPTION OF THE DRAWINGS

The invention can be more fully understood from the following detailed description taken in conjunction with the accompanying drawing, in which:

FIG. 1 is a block diagram illustrating a sound management system, according to a first embodiment of the invention.

DETAILED DESCRIPTION OF THE PREFERRED EMBODIMENTS

Referring to FIG. 1 and according to a first embodiment of this invention, a sound-management system 10 is schematically illustrated and includes sound generator 12, power supply 14, sound controller 16, and sound output device 18. Sound output device 18 may be any of several devices, including open speakers, headphones, bone-conduction transducers, vibration generators and any other device that is able to convert electrical signal into a corresponding sound wave that can be heard or felt by a user in a particular environment. Applicants consider use of headphones to be a preferred sound output device for this invention.

Sound generator 12 produces sound, either structured, such as music, or random noise, such as "pink noise." The sound can either be pre-recorded and provided as sound or music files (stored on an appropriate memory), or can be a circuit-based device that includes electrical components that are arranged to generate electronic "noise" and other electrical components that provide various filters for altering the generated noise prior to outputting the signal to a sound output device 18. As is well known by those of ordinary skill in the art, depending on the specifics of the filtering circuitry various types of noise can be created, such as "white", "brown", "grey", "violet", "blue", and "pink." Each type of "noise" has different sound characteristics, as described below:

White:

White noise is a signal made of uncorrelated samples, such as the numbers produced by a random generator. When such randomness occurs, the signal will contain all frequencies in equal proportion and its spectrum will turn flat. Most white noise generators use uniformly distributed random numbers because they are easy to generate. Some more expensive generators rely on a Gaussian distribution, as it represents a better approximation of many real-world random processes. To the human auditory system, white noise sounds much brighter than what one would expect from a "flat" spectrum. This is because human hearing senses frequencies on a logarithmic scale (the octaves) rather than a linear scale. On the logarithmic scale, white noise packs more energy in the higher octaves, hence its bright sound. White noise sounds similar to TV channel static or "snow."

Brown:

"Brown" noise (also called "red" noise) is a random signal that has been filtered in order to generate a lot of energy at low frequencies. Its power density is inversely proportional to $f^2$ and decreases by 6 dB per octave. Brown noise produces a much warmer tone than white noise (0 dB/oct) or pink noise (−3 dB/oct). Brown noise packs a lot of energy in the lowest frequencies. Each octave packs as much energy as the two octaves above it. For example, the 20 Hz bandwidth between 20 Hz and 40 Hz (one octave) will contain the same sound power as the 120 Hz bandwidth between 40 Hz and 160 Hz (the next two octaves). Brown noise is very relaxing to listen to—sounding similar to powerful ocean waves.

Grey:

Although white noise plays equally loudly at all frequencies, it fails in giving the listener such a perception, because of psychoacoustics. Grey noise is created by passing white noise through a filter to invert the frequency sensitivity curve. As a result, grey noise sounds relatively flat—a bit like muffled white noise.

Violet:

Violet noise is known as differentiated white noise, due to its being the result of the differentiation of a white noise signal. Violet noise generates very high energies at higher frequencies. Its power density is proportional to $f^2$ and increases by 6 dB per octave. Violet noise is also referred to as purple noise. This noise is sharp and not very soothing to listen to unless the volume is very low.

Blue:

Blue noise is a random signal that has been filtered in order to generate higher energies at higher frequencies. Its power density is proportional to the frequency and increases by 3 dB per octave.

Blue noise is also referred as azure noise and packs a lot of energy in the highest frequencies: each octave packs as much energy as the two octaves below it. Blue noise sounds very sharp and is not very soothing to listening to.

Pink:

Pink noise has a spectral envelope that is not flat within a frequency but rolls off at higher frequencies. Pink noise has a greater relative proportion of low frequency energy than white noise and sounds less "hissy."

To the human auditory system—which processes frequencies logarithmically—pink noise is supposed to sound even across all frequencies, and therefore best approximates the average spectral distribution of music. In practice however, it turns out that human ears are more sensitive to certain frequencies, such as in the 2-4 kHz range. Pink noise, despite its even frequency distribution in the logarithmic frequency scale, is perceived as "colored", with a prominent peak perceived around 3 kHz.

Pink noise is a random signal, filtered to have equal energy per octave. In order to keep the energy constant over the octaves, the spectral density is required to decrease as the frequency (f) increases ("1/f noise"). In terms of decibels, this decrease corresponds to 3 dB per octave on the magnitude spectrum.

A basic electronic noise-generating circuit is understood by those of ordinary skill in the art of electronics and the circuit details of such a circuit are generally beyond the scope of this invention. Of course, as is understood by those skilled in the art, that different filter components will create different types of "noise", including the several color types noise types listed above.

Referring again to FIG. 1, and according to one embodiment of the present invention, sound generator controller 16 is connected to sound generator 12 and includes appropriate circuitry that causes sound generator 12 to either:

A) change the type of sound being outputted to sound output device 18; and/or B) change a sound characteristic of the sound being outputted to sound output device 18, in response to receipt of input signal 20.

The term "sound characteristic", includes volume or loudness, timbre, harmonics, rhythm, and pitch. The term "type of sound" refers to sound that is either random noise or structured sound, such as music. An example of "changing the type of sound" can be changing the outputted noise from pink to grey, or white to blue, etc., again in response to receipt of input signal 20. Another example of "changing the type of sound" can be simply changing the song or the genre of music being played, in response to receipt of input signal 20.

As is well understood, all circuitry described herein will be powered by an appropriate power supply 14, which is electrically connected to the circuitry, as required.

In operation, sound management system 10 can be incorporated into an environment for the purpose of managing nearby sounds through masking techniques. As mentioned above, the environment can be very small and controlled, such as a user wearing headphones, larger, such as a desk, or huge, such as a large room including several workers and desks. For the purpose of explanation however, Applicants are considering the environment to be small and controlled—headphones.

Headphones 18 are connected to sound generator 12, which is, in turn connected to sound generator controller 16. As a user works, he or she wears the headphones while a predetermined electronic sound is played through the headphones. The user will enjoy "sound protection" within the surrounding environment (outside the headphone area) because the electronic noise playing in his or her ears will effectively mask any outside noises from reaching his or her ears. In this arrangement, people located nearby the worker can carry on a conversation without the worker hearing them.

According to a first embodiment of the present invention, the user (the person wearing the headphones) can create an input signal 20 that can, in turn, cause sound generator controller 16 to cause sound generator 12 to change the type of electronic sound being played in the headphones, or a sound characteristic of the sound being played in the headphones. The input signal can be created manually (for example, by simply pressing a switch), or automatically, in response to detection of a change of a preset condition. Examples of preset conditions include:

a) Detection of a change of software program being used by the worker;

b) At preset times during the day (such as every hour);

c) At random times throughout the day;

d) Upon detection of changes of the level of ambient noise measured in the room (such as by a microphone);

e) Detection of the user changing their position (such as sitting down from standing, or standing up from sitting);

f) Detection of a change of height of a sit/stand desk being used by the user;

g) Detection of changes of energy levels of the user (e.g., change in measured heart rate); and h) Changes in measured ambient temperature readings.

By way of example, as a user "surfs the web", a certain type of sound and sound characteristic will play in the user's headphones. If the user then starts to read an article, for example, or review spreadsheets, the present sound management system 10, according to the present invention will automatically detect this change in type of work and will change either the type of sound being played on the headphones, or change some sound characteristic. The present sound management system 10 can use a simple algorithm to compare the type of programs that are being used by the user on their computer with a prescribed list to help select an appropriate (or predetermined) type of sound and an appropriate sound characteristic for the particular detected work or task.

In some instances, sound management system 10 can predict what type of work the user is doing while surfing the Internet by detecting level of activity. For example, the present system can measure mouse movement to decide the type of music the user would benefit from. If the user is actively using his or her mouse (or other input device) and actively clicking on links as they surf, then one type of music could be playing in the user's headphones, for example, an upbeat, high-energy type of music. However, if it is later determined that the mouse-use has stopped (or less clicks per minute are detected), then sound management system 10 may decide that it is likely the user is now reading or reviewing a selected article or webpage and may then change the type of music to benefit that particular activity, such as changing the music to something more soothing so the user can better concentrate on the article or webpage.

By way of another example, when the present sound management system 10 is used in combination with a motorized sit/stand desk, such as one commercially available by Stirworks, Inc, of Pasadena, Calif., USA (www.Stirworks.com), accelerometers or other appropriate sensors located in the desk can be used to predict the type of work the user is doing. Perhaps the present system is programmed (following the setup by the user) to change the music from soothing when the desk is at the "sit" height to high-energy when the desk moves to the "stand' height. Also, vertical displacement frequency of desk movement and desk-height duration at certain heights can be used to predict the level of stress or fatigue of the user and can thereby select the best type of sound and sound characteristic to benefit the user and mitigate the effects of the stress and fatigue.

Other sensors that can be used as input signals for controlling the selected type and characteristic of the sound, according to this invention, include the user's computer (as it's being used), any electronic wearable device, such as a health-monitoring device (for measuring a user's blood pressure, body temperature and heart-rate and level of accumulative and recent activity, a microphone, a thermal sensor, a camera, a touch screen input device, and a computer mouse. These sensors, used alone or in combination can detect levels of stress, fatigue and activity which in turn, can be used to control the type of sound and its characteristic. Sound management system 10 can use this collected information to tune the music, for example, or the type of noise to "match" the measured type and level of work or stress. If the work is determined to be something like Internet surfing, or sketching, etc., the music selected can be active (e.g., rock) and its characteristic can increase in tempo and/or volume.

If the work is determined to be more stressful, perhaps indicated by a measured higher heart-rate of the user, then the music type could be more relaxing, such as jazz or classical, or the type of sound could be changed to an appropriate soothing background noise, such as quiet brown noise.

If sound management system 10 determines or predicts that the user is reading or doing an activity that requires focus and comprehension, then the system will automatically decrease the volume and tempo and select music (or other) that includes no words or lyrics.

The present system can also use microphones (not shown) to measure external noise and other potential audible distractions located within ear-shot of the user and then moderate the overall volume and type of sounds played to the user in an effort to mask or at least mitigate the level of distraction that these nearby sounds may have on the user.

The sounds that are sent to the user's ears may be sent through headphones that the user wears, or may be sent via nearby speakers, including speakers that are incorporated into the construction of the desk itself (i.e., embedded).

When the present sound-management system 10 is used in combination with a work-desk, the system can "listen" to the local environment and use the measured information to adjust the type of white noise or music played to the user's ears and the characteristics of that noise or music. As the level of measured audible distractions in the environment increase, the amplitude of the noise or the music sent to the user's ears likewise increases, but only up to a point. If the "corrective" noise or music sent the user's ears becomes too loud, at some point, this corrective sound itself will become a distraction to the user.

As described above, various "colors" of noise are predetermined and controlled spectrums of sound. According to another embodiment of the present invention, sound management system 10 can create its own specific noise with specific spectrum characteristics based on the tones the system detects around the user and the user's desk. For example, if the present system detects a person nearby speaking in a low voice, the system can introduce a type of music or sets of tones (or other generated custom noise) that are in a similar tonal range as the nearby distracting voice. By matching the audible distraction with similar tones (preferably of noise or sounds without words or lyrics), the distracting conversion will become effectively masked and the user's brain will not bother to try to understand it, thereby keeping the user focused and unbothered. This allows the system to abate or mitigate the distracting sounds and lower the Articulation Index without having to generate a full spectrum of noise.

Similarly, if a high squeaking noise is detected by the system of the present invention, a noise that is generated perhaps from a nearby door opening and closing, the generated corrective noise produced by the present system for the user's ears could be instantly shifted in that direction on the sound spectrum, functioning similar to a conventional active noise-cancellation system. By focusing on correcting or balancing the detected and measured frequency spectrum signature of the nearby distraction, the distracting noise can effectively be mitigated without a noticeable increase in amplitude in the user's ears.

System can be moved from random noise (white, pink, etc) to music using local controls (touch screen, etc).

If the user is wearing a device that measures levels of energy expenditure (such as a Fitbit® device, which is manufactured by Fitbit, Inc. of San Francisco, Calif., USA), the present sound management system will be able to "read" the Fitbit® device and change the type of music in response to the data read. For example, if the user recently completed a lot of exercise, the present sound management system 10 will change the music being played in the user's headphones to perhaps something more upbeat to make sure that the user doesn't fall asleep.

The user may have control of the present sound-management system to override any music or noise that the system automatically creates, and select their own from a list of selections, both of music and different "colored" noises. The user can also adjust other characteristics of the generated sounds, as desired. The user can make these adjustments using an appropriate controlling device, such as a computer with a touch-screen, or perhaps a tablet, or smart phone. Sound management system 10 is also able to automatically mix in music with any of the colored noises so that if a user is listening to white noise for an hour or so, for example, the present system can automatically and preferably slowly mix in the sounds of recognizable music. This will allow the user to avoid getting sick of listening to random noise for long periods of time. After a prescribed period of time, the system can slowly blend other noise patterns to create an effective sound that helps the user to abate or mitigate nearby audible distractions. Sound management system 10 allows the user a little variety in the sounds being played.

According to another embodiment of the invention, sound management system 10 includes a wireless connection (or a direct wired connection) to a user's computer or smart phone and is able to play specific sounds, such as music, in response to information on the user's calendar. For example, if it is shown on the user's calendar that the user has some free time between 3:00 and 3:30, the present system can play some upbeat music or some of the user's favorite songs. If the user will be going to a concert later that evening to see a particular band, the system will be able to obtain details of the band and the time an event of the concert from the user's smart phone, for example and then use this information to play select songs by that band . . . to get the user in the right "mood" for the concert later that night. Similarly, the user may be traveling to a country soon, such as Mexico, and the present system will learn this from the connected smart phone or computer and perhaps play Mexican music and sounds at different moments leading up to the day of travel. The system will learn what music and specific songs and sounds that the user likes (by keeping track of the frequency of which certain songs and sounds are played) and will play one or more of these preferred songs or sounds for the user at a specific time during the day and week. The present system will remember that the user loves to hear a particular song on Fridays at a given time and will play that song when the internal clock indicates that exact time and day.

The present system can detect which application the user is using on his or her computer or smart phone and could play sounds or music that are specific to particular detected applications. For example, when the user logs into Facebook®, the present system will detect this and will start playing a specific set of music tracks, perhaps "fun" and upbeat music, since the system will assume that the user is taking a break from work to enjoy reading their "wall."

Also, the present system can read inputs or profile data or favorite song lists generated by music programs, including Spotify® and Pandora®, and use this information and biometric data to help select new sounds and music to be played for the user at different times.

The present system is adapted to absorb any reachable information that provides context, such as where the user has been, what the user has been doing, and perhaps where the user will be going in the future. The system can then use this information to help select the types of music and sounds appropriate for the user, given other information, such as time of day, and other environment and biological conditions, described above.

The present system can use immediate user feedback to help learn what the user likes and dislikes and use this information to help plan future sounds and music. For example, if the system selects a song and the user turns the music off or skips the song, or turns the music down, then the system will know that it selected a song or sound that you likely do not like. It will then remove this particular song from the primary song list and move it to a secondary list. At random times, the system can play the song again from the secondary list and see how the user responds. If the response is still negative, the system will move the song to the "no-play" folder, where it will remain until the user moves it back to the primary list.

According to another feature of the present invention, in a work environment where there are several desks, each using the present sound management system 10, the system can work with all the users by allowing each to effectively vote on the sound being played, either a random noise or a particular song, and cause the system to accommodate the played sounds and music based on the consensus vote. The voting could be inputted by touch screen connected to a smart phone or computer that his connected to the system 10 by WIFI or other appropriate connection.

Also, each desk could include a microphone, as mentioned above, wherein all microphones would be connected to the sound management system 10. According to this feature, the microphones could be used to collect distracting sounds (sound levels at different frequencies). This information could be used to determine which areas within a work environment are quiet and which are loud. Workers could then move about within the environment to find the best work zone based on this information. This information would be sensitive to time and would be dynamic but it is likely that trends could be formed to establish zones within the work environment that offer average quiet and average moderate sounds within a range of volume and frequency that is considered distracting.

What is claimed is:

1. A sound management system for use with a sit-stand desk including a height adjustable work surface, the sound management system comprising:
    a memory device for storing a plurality of sounds including at least a first sound and a second sound, wherein the first sound is audibly different than the second sound; and
    a controller for selecting at least one of the plurality of stored sounds as a selected sound based on at least a first input signal, the first input signal and the corresponding selected sound being generated at least in part as a function of a height of the sit-stand desk;
    wherein said controller sends a command to a speaker to audibly generate said selected sound; and
    wherein the speaker is controlled to generate the selected sound until some other measured condition occurs; and
    wherein the controller selects the selected sound based on the first input signal and at least a second input signal that is different than the first input signal, the second input signal generated at least in part as a function of a change in a measured biological condition of a user and wherein said measured biological condition of said user is user-fatigue.

2. The sound management system of claim 1, wherein said user-fatigue is determined by calorie expenditure of recent physical activity of said user.

3. The sound management system of claim 1, wherein said first sound is one of music and random noise.

4. The sound management system of claim 1, wherein said second sound is one of music and random noise.

5. The sound management system of claim 1, wherein said first sound is a combination of music and random noise.

6. The sound management system of claim 1, wherein said speaker is a set of headphones worn by the user.

7. The sound management system of claim 1, wherein said speaker is built into said sit-stand desk.

8. The sound management system of claim 1 wherein said controller is further configured to select one of the plurality of stored sounds as a selected sound in response to at least a first statistic related to the height of the work surface.

9. The sound management system of claim 8, wherein said first sound is one of music and random noise and said second sound is the other of music and random noise.

10. The system of claim 8 wherein the statistic related to height includes instantaneous height of the work surface.

11. The system of claim 8 wherein the statistic related to height includes duration of time that the work surface is at a current height.

12. The system of claim 8 wherein the statistic related to height includes frequency of work surface height adjustment.

13. The sound management system of claim 1 wherein the other measured condition includes a change in the height of the sit-stand desk.

14. The sound management system of claim 13 wherein the selected sound includes a sound type, the system further including at least one ambient condition sensor, the controller further controlling at least one characteristic of the sound type based on information from the ambient condition sensor.

15. The sound management system of claim 14 wherein the at least one characteristic includes at least one of volume, loudness, timbre, harmonics, rhythm and pitch.

16. A sound management system for use with a sit-stand desk including a height adjustable work surface, the sound management system comprising:
a memory device for storing a plurality of sounds including at least a first sound and a second sound, wherein the first sound is audibly different than the second sound; and
a controller for selecting at least one of the plurality of stored sounds as a selected sound based on at least a first input signal, the first input signal and the corresponding selected sound being generated at least in part as a function of a height of the sit-stand desk;
wherein said controller sends a command to a speaker to audibly generate said selected sound;
wherein the speaker is controlled to generate the selected sound until some other measured condition occurs; and
wherein the controller selects the selected sound based on the first input signal and at least a second input signal that is different than the first input signal, the second input signal generated at least in part as a function of a change in a measured biological condition of said user and wherein said measured biological condition of said user is user-stress.

17. The sound management system of claim 16, wherein said user-stress is determined by one of body temperature, blood pressure, and heart rate.

18. A sound management system for use with a sit-stand desk including a height adjustable work surface, the sound management system comprising:
a memory device for storing a plurality of sounds including at least a first sound and a second sound, wherein the first sound is audibly different than the second sound; and
a controller for selecting at least one of the plurality of stored sounds as a selected sound based on at least a first input signal, the first input signal and the corresponding selected sound being generated at least in part as a function of a height of the sit-stand desk;
wherein said controller sends a command to a speaker to audibly generate said selected sound; and
wherein the speaker is controlled to generate the selected sound until some other measured condition occurs; and
wherein the controller selects the selected sound based on the first input signal and at least a second input signal that is different than the first input signal, the second input signal generated at least in part as a function of a change in an environment of a user of the sit-stand desk, and wherein said change in said environment is one of a change in ambient temperature, a change in ambient noise level, or a change in type of a software program in use by the user.

19. A sound management system for use in a work space, the sound management system comprising:
a memory device for storing a plurality of sounds, wherein each sound is audibly different than the other sounds in the plurality of sounds; and
a controller for selecting at least one of the plurality of sounds as a selected sound in response to at least first and second different input signals;
wherein said controller sends a command to a speaker to audibly generate said selected sound; and
wherein said first input signal is generated at least in part as a function of a change in a measured biological condition of a user and the second input signal is generated at least in part as a function of a measured non-biological condition is a sensed height of a height adjustable sit-stand desk;
wherein the speaker is controlled to generate the selected sound until some other measured condition occurs;
wherein the measured non-biological condition is a sensed height of a height adjustable sit-stand desk.

20. The sound management system of claim 19, wherein said measured biological condition is user fatigue.

21. The sound management system of claim 19, wherein said measured condition other than a biological condition is activity level in the workspace.

22. The sound management system of claim 21, further including at least a first sensor for sensing activity level.

23. The system of claim 21 wherein the activity level is activity level of a computer associated with user.

24. The sound management system of claim 19, wherein said measured biological condition is user stress level.

25. The sound management system of claim 19, wherein said speaker is a set of headphones worn by a user.

26. The sound management system of claim 19, wherein at least a first sound in the plurality of sounds is one of music and random noise and at least a second sound in the plurality of sounds is the other of music and random noise.

27. The sound management system of claim 19 wherein the measured biological condition is a current posture of the user.

28. The sound management system of claim 19 wherein the measured condition other than a biological condition includes environmental sound within the ambient work space.

29. The sound management system of claim 19 wherein the selected sound is a specific sound type based on one of the first and second measured conditions, the system further adjusting at least one sound characteristic of the specific sound type based on the other of the measured conditions.

30. The sound management system of claim 29 wherein the specific sound type is based on the first measured condition.

31. The system of claim 19 wherein the measured condition other than a biological condition includes detection of an application accessed by the user.

32. The system of claim 19 wherein the measured condition other than a biological condition includes detection of an event on the user's schedule.

* * * * *